United States Patent
Koehler et al.

(10) Patent No.: US 10,902,648 B2
(45) Date of Patent: Jan. 26, 2021

(54) ROBUST RECONSTRUCTION FOR DARK-FIELD AND PHASE CONTRAST CT

(71) Applicant: KONINKLIJKE PHILIPS N.V., Eindhoven (NL)

(72) Inventors: Thomas Koehler, Norderstedt (DE); Bernhard Johannes Brendel, Norderstedt (DE); Peter Noel, Unterföhring (DE); Franz Pfeiffer, Unterföhring (DE); Maximilian Von Teuffenbach, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 178 days.

(21) Appl. No.: 15/736,975

(22) PCT Filed: Jun. 27, 2016

(86) PCT No.: PCT/EP2016/064799
§ 371 (c)(1),
(2) Date: Dec. 15, 2017

(87) PCT Pub. No.: WO2016/207423
PCT Pub. Date: Dec. 29, 2016

(65) Prior Publication Data
US 2018/0182131 A1    Jun. 28, 2018

(30) Foreign Application Priority Data

Jun. 26, 2015    (EP) .................................... 15173981

(51) Int. Cl.
*G06T 11/00*     (2006.01)
*A61B 6/00*     (2006.01)

(52) U.S. Cl.
CPC .......... *G06T 11/006* (2013.01); *A61B 6/4208* (2013.01); *A61B 6/5205* (2013.01); *G06T 2211/424* (2013.01)

(58) Field of Classification Search
CPC ............. G06T 11/006; G06T 2211/424; A61B 6/4208; A61B 6/5205
See application file for complete search history.

(56) References Cited

U.S. PATENT DOCUMENTS

| 4,637,040 A | 1/1987 | Sohval |
| 7,889,355 B2 * | 2/2011 | De Lega ............ G01B 9/02087 356/511 |

(Continued)

OTHER PUBLICATIONS

Google Scholar Search Results.*

(Continued)

*Primary Examiner* — Qun Shen
(74) *Attorney, Agent, or Firm* — Larry Liberchuk

(57) ABSTRACT

A system and related method for signal processing. Interferometric projection data reconstructed into one or more images for a spatial distribution of a physical property of an imaged object. The interferometric projection data is derived from signals acquired by an X-ray detector (D), said signals caused by X-ray radiation after interaction of said X-ray radiation with an interferometer and with the object (OB) to be imaged, said interferometer (IF) having a reference phase. A reconstructor (RECON) reconstructs for the image(s) by fitting said data to a signal model by adapting fitting variables, said fitting variables including i) one or more imaging variables for the one or more images and ii), in addition to said one or more imaging variables, a dedicated phase variable for a fluctuation of said reference phase.

11 Claims, 3 Drawing Sheets

(56) References Cited

U.S. PATENT DOCUMENTS

| | | | |
|---|---|---|---|
| 7,889,838 B2 | 2/2011 | David | |
| 8,218,152 B1* | 7/2012 | Marks | G01N 21/45 356/479 |
| 2005/0055184 A1* | 3/2005 | Barbour | G06T 5/003 703/2 |
| 2009/0092227 A1* | 4/2009 | David | A61B 6/4233 378/36 |
| 2009/0125242 A1* | 5/2009 | Choi | G01N 21/51 702/19 |
| 2010/0220834 A1* | 9/2010 | Heismann | A61B 6/482 378/19 |
| 2012/0153182 A1* | 6/2012 | Iwakiri | A61B 6/5205 250/394 |
| 2012/0307966 A1* | 12/2012 | Roessl | A61B 6/00 378/16 |
| 2013/0011040 A1* | 1/2013 | Kido | A61B 6/4291 382/132 |
| 2013/0032727 A1* | 2/2013 | Kondoh | G01N 23/046 250/394 |
| 2013/0289394 A1* | 10/2013 | Hielscher | A61B 5/0053 600/425 |
| 2014/0050382 A1* | 2/2014 | Adie | G02B 21/0056 382/131 |
| 2014/0226782 A1 | 8/2014 | Stutman | |
| 2014/0226783 A1* | 8/2014 | Ning | A61B 6/032 378/5 |
| 2016/0231258 A1* | 8/2016 | Wen | G01N 23/04 |

OTHER PUBLICATIONS

Pfeiffer et al, Phase Retrieval and Differential Phase-Contrast Imaging with Low-Brilliance X-Ray Sources, Nature Physics, vol. 2, No. 258, 2006.

Momose et al "Four-Dimensional X-Ray Phase Tomography with Talbot Interferometry and WHite Synchrotron Radiation: Dynamic Observation of a Living Worm", Optics Express vol. 19, No. 9, 2011.

Miao et al "Motionless Phase stepping in X-Ray Phase Contrast Imaging with a Compact Source", PNAS, vol. 110, No. 48, pp. 19268-19272, 2012.

Ritter, Andre et al "Simultaneous maximum-likelihood reconstruction for x-ray grating based phase-contrast tomography avoiding intermediate phase retrieval", Jul. 30, 2013.

Brendel, Bernhard et al "Intensity-Based Iterative Reconstruction for Differential Phase-Contrast Imaging with Reconstruction Parameter Estimation", 13th International Meeting on Fully 3D Image Reconstruction in Radiology and Nuclear Medicine, pp. 713-716, 2015.

Hahn, Dieter et al "Statistical Iterative Reconstruction Algorithm for X-Ray Phase-Contrast CT", Scientific Reports, Jun. 2015, p. 10452.

Zanette, I. et al "Trimodal Low-Dose X-Ray Tomography", PNAS, vol. 109, No. 26, pp. 10199-10204, 2012.

* cited by examiner

ROBUST RECONSTRUCTION FOR DARK-FIELD AND PHASE CONTRAST CT

CROSS-REFERENCE TO PRIOR APPLICATIONS

This application is the U.S. National Phase application under 35 U.S.C. §371 of International Application No. PCT/EP2016/064799, filed on Jun. 27, 2016, which claims the benefit of European Patent Application No. 15173981.0, filed on Jun. 25, 2015. These applications are hereby incorporated by reference herein.

FIELD OF THE INVENTION

The invention relates to a signal processing system, to a signal processing method, to an imaging arrangement, to a computer program product, and to a computer readable medium.

BACKGROUND OF THE INVENTION

Grating-based differential phase-contrast imaging is an emerging and promising approach to improve X-ray computed tomography. In addition to the spatial distribution of the linear attenuation coefficient, this method provides access to the spatial distribution of the electron density (via refraction) and of the small-angle scattering power of the object.

In one system setup, three gratings are placed additionally in a radiation beam generated by the imager. One basic requirement for data acquisition is that data with different relative positions of the gratings need to be acquired. This is traditionally achieved by a so-called "phase-stepping" or "fringe-scanning" procedure, in which one of the gratings is shifted sideways between successive detector readings. See for instance, Pfeiffer et al., Phase retrieval and differential phase-contrast imaging with low-brilliance X-ray sources, nature physics 2, 258 (2006).

Various alternative approaches have been proposed to avoid gratings movement as in phase stepping. One alternative is the Fourier-transform method, described for instance in Momose et al., Four-dimensional X-ray phase tomography with Talbot interferometry and white synchrotron radiation: dynamic observation of a living worm, Optics Express 19(9), 8423 (2011). In this approach, the gratings are purposely detuned such that a fringe pattern with a period of a few detector pixels is achieved. The phase of the fringe pattern is determined by analysis of neighboring detector pixels. Another approach is focal spot sweeping. As in the Fourier transform method, a fringe pattern of sufficient frequency is produced on the detector. However, the phase is obtained by focal spot deflection. See for instance, Miao et al., Motionless phase stepping in X-ray phase contrast imaging with a compact source, PNAS 110(48), 19268 (2012).

However, it has been observed by Applicant that these and other methods are not very robust to environmental changes for instance.

SUMMARY OF THE INVENTION

There may therefore be a need in the art for an alternative image processing method or related system.

The object of the present invention is solved by the subject matter of the independent claims where further embodiments are incorporated in the dependent claims.

It should be noted that the following described aspects of the invention equally apply to the image processing method, to the imaging arrangement, to the computer program product, and to the computer readable medium.

According to a first aspect of the invention, there is provided a signal processing system, comprising:

an input port for receiving interferometric projection data derived from signals acquired by an X-ray detector, said signals caused by X-ray radiation after interaction of said X-ray radiation with an interferometer and with an object to be imaged, said interferometer having a reference phase;

a reconstructor configured to reconstruct one or more images of a spatial distribution of one or more physical properties of said object, the reconstructor configured to fit said interferometric projection data to a signal model by adapting a plurality of fitting variables, said fitting variables including i) one or more imaging variables for the one or more images and ii), in addition to said one or more imaging variables, a dedicated phase variable for a fluctuation of said reference phase; and an output port for outputting said one or more images.

The physical properties of main interest herein are attenuation, refraction and small angle scattering. The latter has been found to relate to micro-structures in the imaged object.

According to one embodiment, the projection data has been acquired from different projection directions such as in CT or tomosynthesis.

The fluctuation or "offset" of the reference phase can be modelled spatially and/or temporally.

Specifically, according to one embodiment, the reference phase fluctuation is modelled by said phase variable as a constant offset independent of said different projection directions.

According to one embodiment, the reference phase fluctuation is modeled by said phase variable as a non-constant offset that depends on said different projection directions.

According to one embodiment, the reference phase fluctuation is modeled by said phase variable to depend on a position of a detector element of said X-ray detector. Said differently, the reference phase fluctuation is modeled by said phase variable to vary across detector elements of said detector.

According to one embodiment, said detector element is a single detector pixel or group of pixels such as a detector module. In other words, the fluctuation is modelled to depend on pixel position so can vary from pixel to pixel (but not necessarily over all pixels) across the detector. Alternatively, there is only pixel-group dependency. In other words, the phase variable depends on pixel-group position rather than on individual pixel positions. One pixel group may be for instance a respective one of the detector modules. In one embodiment, the offset within each or some or all detector modules is constant but may differ from detector group to detector group.

According to one embodiment, the phase variable includes instead or in addition to a spatial dependency, a temporal dependency to model a change over time of said fluctuation.

In sum, what is proposed herein is a robust concept for data acquisition and image reconstruction in interferometer (e.g. grating) based (differential) phase contrast imaging and/or interferometer (e.g. grating) based dark field imaging. Robustness is achieved by mathematically modelling the drift of fringes during the acquisition and by fitting the model parameters during reconstruction concurrently with the imaging variables. Better robustness helps reducing image artifacts.

In particular increase in robustness has been observed by Applicant with the proposed method. In particular, the proposed method is less sensitive to drift or vibration-induced variations of the fringe phase which cause a change in the reference phase. It is precisely these fluctuations that are caused by mechanical (even or thermal) influence that the proposed system can account for. The requirement for a high reproducibility of the fringe pattern between the air scan (calibration measurements) and the object scan can be lowered. As a consequence of the proposed method, fewer air scans may be required because the proposed system has been observed to account for or even correct (during iterative reconstruction) wrong or inaccurate calibration data.

The present invention allows for useful application in (differential) phase contrast imaging as well as dark field imaging. More specifically, the present invention allows for useful application in a clinical environment such as a hospital. That is, the present invention is very suitable for application in imaging modalities such as computed tomography (CT) for the medical examination of patients. In addition, the present invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

BRIEF DESCRIPTION OF THE DRAWINGS

Particular aspects of the present invention will now be explained with reference to the examples described hereinafter in connection with the accompanying drawings in which identical parts are designated in the same manner.

DETAILED DESCRIPTION OF EMBODIMENTS

Figure 1:
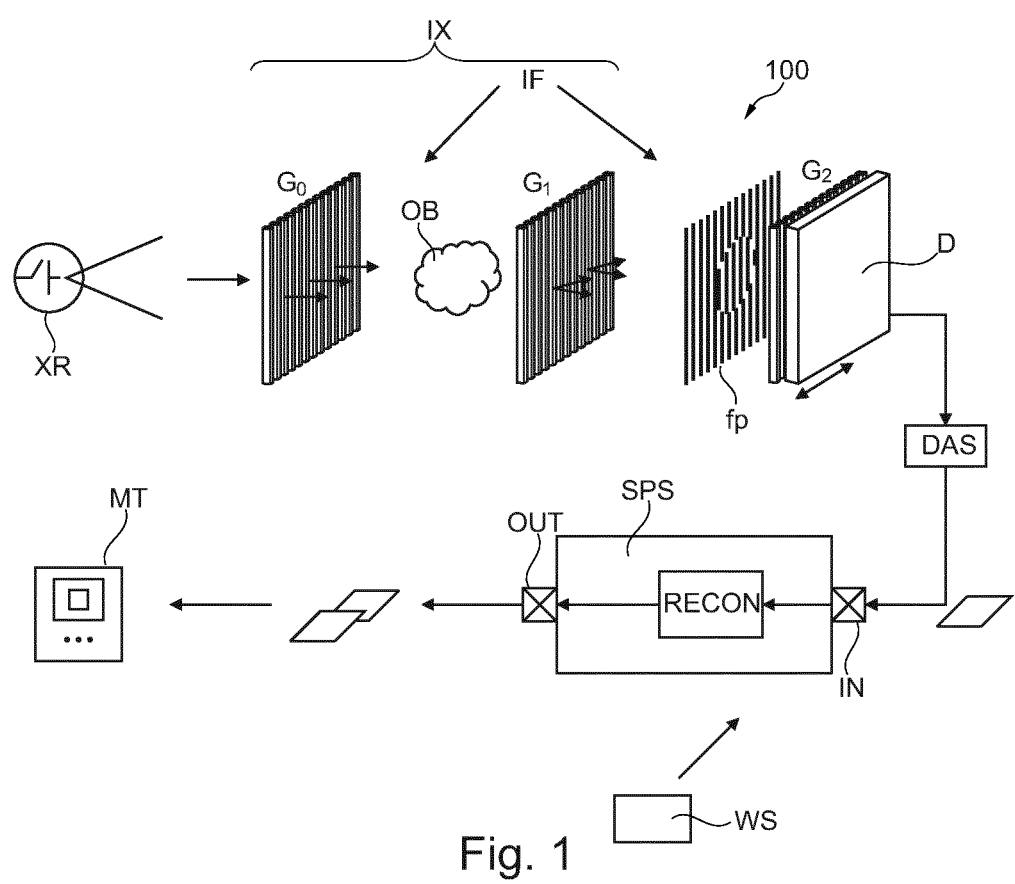
FIG. 1 shows a block diagram of an imaging arrangement.

With reference to FIG. 1, there is shown a schematic block diagram of an imaging arrangement 100. Broadly, the imaging arrangement includes an X-ray imaging apparatus ("imager") IX including an interferometric arrangement IF.

The interferometric arrangement IF includes one or two gratings arranged between the X-ray source XR and a detector D. There is an examination region between the X-ray source and the detector and between at least two of the gratings.

The imaging or examination region is suitable to receive an object OB to be imaged. The object is animate or inanimate. An animate object includes for instance an animal or human patient or at least a part thereof (region of interest) to be imaged.

X-ray radiation emitted from a focal spot of X-ray source XR interacts with the gratings of the interferometer IF and the object and is then incident on the radiation sensitive surface of detector D formed by a plurality of detector pixels. The incident radiation causes electrical signals which are picked up by a data acquisition unit DAS and are converted into digital projection data. Because of interaction with the interferometer IF (more of which further below), this projection data is referred to herein as interferometric projection data.

The interferometric projection data is then processed in a manner to be described in more detail below by a signal processing (sub-)system SPS to produce output images which can then be stored on a data base and/or can be rendered for view on a monitor MT or can be otherwise image processed.

The signal processing sub system SPS may run as a software routine on a workstation WS. The workstation WS on which the signal processing sub system SPS is installed may be arranged to receive the projection data in a wireless or a wired network from the imager IX The projection data may be received as they are supplied by the imager or they may be received later from a memory of database. The work station may not necessarily be associated with the imager IX as the proposed signal processing sub system SPS may be run on essentially any general purpose computing device and the projection data can be supplied thereto for instance by a memory dongle via USB (universal serial bus) or by any other suitable interface.

Preferably, the imager IX is arranged as a tomographic imaging apparatus the optical axis which is shown in a horizontal arrangement running from the focal point of the X-ray source to the detector. This axis can be changed so as to acquire projection data from multiple projection directions around the object (not necessarily in a full revolution, a 180° rotation may be sufficient, or even less in tomosynthesis, etc.). The object OB is thought to reside at an iso-center in the examination region whilst at least the X-ray source (in some embodiments together with the detector) and some or all of the interferometer rotates around the object in a projection data acquisition operation. The projection data can be processed, more specifically can be reconstructed, by the signal processing sub system SPS into cross sectional images revealing the internals of the object OB. By advancing the object through the examination region, multiple cross sectional images can be obtained which can be combined together to form a 3D image volume of the object.

The imager IX is capable of producing phase contrast and/or dark field (cross section) images. In some embodiments, but not necessarily in all embodiments, there is also a third image channel for a conventional attenuation (cross section) image. The attenuation image represents spatial distribution of attenuation coefficient across the object in the respective section plane, whilst the phase contrast and the dark-field images represent spatial distribution of refractive activity of the object and small angle scattering (caused by micro structures in the object), respectively. Each of these images may have diagnostic value for a given diagnostic task at hand.

The capability of imaging for phase contrast and/or dark field signals comes about by operation of the interferometer IF. The interferometer IF comprises in one embodiment two gratings G1 (sometimes referred to a phase grating) and G2 (sometimes referred to as analyzer grating) arranged at a specific distance to each other. Preferably G2 is an absorber grating and G1 is a phase or absorber grating. In one embodiment, the two gratings are arranged, seen along the optical axis, downstream the examination region (in particular the object OB), so that, during the imaging, the two gratings are situated between the object and the detector. The examination region in this arrangement is then between X-ray source and the grating pack formed by the two gratings G1 and G2. In another embodiment, the two gratings are situated, seen along the optical axis, on opposite sides of the examination region (in particular the object OB).

In case the X-ray radiation is incoherent, there is a source grating G0 arranged between focal spot of the X-ray source XR and the object to increase the coherence of the emitted radiation. The described interferometric set up is that of those that allow Talbot architecture. The distance between G0 and G1 and between G1 and G2 are specifically adjusted according to the Talbot-Lau set up that has been described elsewhere. The distances between G0 and G1 and between G1 and G2 must be finely tuned to fit the requirements of Talbot distance which in turn is a function of the "pitch" (that is, the spatial period of the grating rulings) of the respective grating. As an alternative to the above described interferometer, inverse grating geometries are also envisaged herein where one of the two interferometer gratings (G1) is positioned between the source grating G0 and the examination region whereas the other (G2) is between the examination region and the detector. In other words the examination region is sandwiched between the interferometer IF.

No matter the grating geometry used, assuming for a moment that there is no object OB present in the examination region the coherent radiation emerges on the far side of G0, interacts with the interferometer G1, G2 to produce an interference pattern fp, in particular, fringes of a Moiré pattern, which can be detected at the detector D. To achieve this pattern, the two gratings of the interferometer are slightly de-tuned (for instance by slightly tilting the two gratings G1.G2 relative to each other). This Moiré pattern fp, which we will refer to herein the "reference interference pattern" fp, has a certain fixed reference phase, reference visibility and intensity, all of which are encoded by the reference interference pattern fp. The reference pattern is solely the result of the interferometer's presence (for a given radiation density). In that sense it can be said these quantities, in particularly the reference phase, is a property of the interferometer as such and it is therefore no abuse of language to say that the interferometer "has" said reference phase, said reference intensity and said reference visibility.

Now, if the object to be imaged is introduced into the examination region this object will interact with the coherent radiation to which it is now exposed to, in other words, the coherent radiation will be partly absorbed, refracted and scattered. The result of this object interaction is yet another interference pattern, different from the reference pattern, which will be observed at detector D. The interference pattern induced by the presence of object OB can be understood as a perturbed version of the reference pattern when there was no object present in the examination region. The reference data of the reference interference pattern fp are usually acquired in calibration measurement also referred to as an "air scan". The actual object measurements are then acquired in a second scan when the object to be imaged is present in the examination region. One way to sample the reference pattern is by inducing, during X-ray exposure and for any given position of the optical axis of the scanner IX, a sample motion between the interferometer and the object and/or the X-ray radiation. In this manner, the interferometric projection data it acquired and can then be processed as will be explained in more detail below to extract the sought after images of attenuation, phase contrast and/or dark field. More particularly, this relative sample motion can be introduced for instance by focal spot sweeping or the "phase stepping" technique in which one of the gratings G1 or G2 or G0 is moved relative to the other. In alternative embodiments, the interference pattern can be sampled by sampling across neighboring pixels so no sample motion is required in these embodiments. The upshot of any of these sampling or interference pattern data collections is, that for each projection direction i, a series of measurements are acquired per detector pixel j. In previous approaches this interferometric data had to be processed separately in what is commonly known as a "phase retrieval algorithm" to computationally extract projection data for each of the three channels (phase contrast, attenuation and dark field imaging) and the data so extracted was then reconstructed in the usual manner by a suitable reconstruction algorithm (such as filtered back-projection) FBP for instance or by iterative reconstruction to arrive at the cross sectional images for each of the channels.

In radical departure from this it is proposed herein to use instead an iterative reconstruction algorithm that eliminates the explicit phase retrieval step, operates directly and exclusively on the intensity values as measured at the detector, and, in addition, includes modelling a fluctuation of the reference phase. This is because Applicant has observed that phase contrast and dark field imaging, especially in computed tomography context, may suffer from severe artifacts which are caused by such fluctuations or changes, also known as drifts, of the reference interference pattern. This is especially true in CT where during the rotation buckling and other mechanical changes occur that induce those fluctuations. Also thermal expansion or contraction has been identified to cause these fluctuations. It is therefore proposed herein to not only include fitting variables for the three image channels into a common reconstruction problem but also to include, in addition, a dedicated fitting variable that accounts for the fluctuations of the reference phase to reduce those artifacts mentioned. Indeed, these artifacts in the reconstructed imagery can be thought to arise if the effect caused by the reference phase fluctuation is incorrectly attributed to the other three fitting variables for the three channels. The adoption as proposed herein remedies or at least reduces artifacts because the judicious placement (on which more below) of this dedicated variable for the fluctuations of the reference phase prevents incorrect attribution of this effect to the other variables (absorption, refraction or small angle scattering). Said differently, Applicant proposes to increase the "pool" of fitting variables by introducing said fluctuation variable in a direct reconstruction algorithm to arrive in particular at artifact reduced phase contrast and/or dark-field cross section images.

Broadly, for the reconstruction scheme as implemented by the proposed signal processing component SPS, a reconstruction technique as described for instance by A. Ritter et al in "Simultaneous maximum-likelihood reconstruction for X-ray grating based phase-contrast tomography avoiding intermediate phase retrieval", available online, visit arXiv: 1307.7912 [physics.med-ph], version as per 30 Jul. 2013, can be used. However it will be understood by those schooled in the art that Ritter et al merely provide an example for a possible reconstruction setting within which the proposed system and method can be practiced and other settings are excluded herein.

In Ritter et al and similar iterative reconstruction approaches, the construction problem is formulated as an optimization problem in terms of a cost or objective function. The cost and objective function is made up from data term that records the actually measured interferometric projection data and this is compared against a forward signal model. Additionally, in some embodiments a penalization term or regularizer term is used to enforce certain smoothness properties in space or time, or to incorporate other a-priori information about the unknowns to reconstruct.

In summary then, a signal processing system as proposed herein includes an input port IN for receiving the interferometric projection data converted from signals detected at detector D. This data is then fed into a reconstructor RECON which runs an iterative reconstruction scheme based on the above sketched objective function to produce in one or more iterations the sought after images by fitting variables for these images to the signal model. These fitting variables include, as briefly mentioned above, in addition to the image fitting variables for the three channels, a dedicated fitting variable for the reference phase fluctuation. The reconstructed imagery is then output at output port OUT and can then be stored or viewed or otherwise processed as required.

Figure 2:
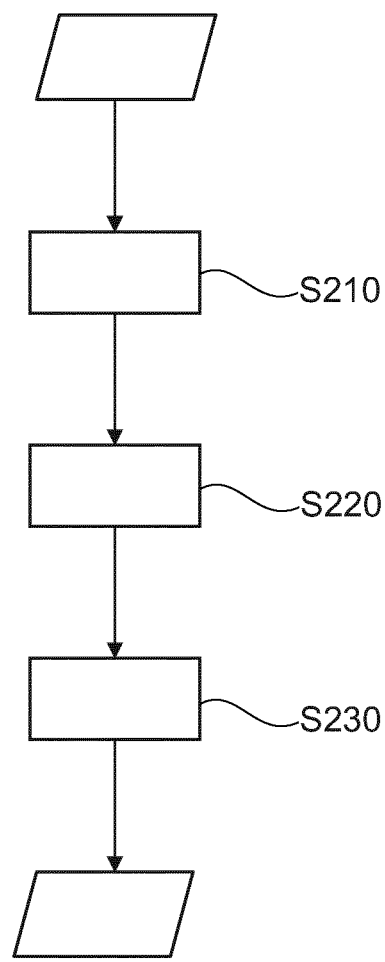
FIG. 2 shows a flow chart of a signal processing method.

Operation of the proposed re-constructor RECON is now explained in more detail with reference to the flow chart in FIG. 2.

At step S210 the interferometric projection data for each projection direction is received.

At step S220, a reconstruction algorithm is then performed based on the optimization of a cost function. More particularly, the reconstruction is formulated as a minimization problem based directly on measured intensities. Yet more specifically, the reconstruction of the linear attenuation coefficient μ (attenuation image), the electron density 6 image (which corresponds, up to a proportionality factor, to the phase contrast image), and the scatter coefficients (dark-field image) is obtained by minimizing the cost function $\Delta^2$:

$$\Delta^2(\mu, \delta, \varepsilon, \psi) = \sum_{i,j} \frac{1}{\sigma_{ij}^2} (J_{i,j} - I_{ij}(\mu, \delta, \varepsilon, \psi))^2 \quad (1a)$$

where i indexes all projection angles (or more generally i is a readout index) and j all pixels of the detector. J denotes measured intensities with statistical variance σ and I denote the forward calculated intensities according to the following forward signal model for the measured densities:

$$I_{ij}(\mu,\delta,\varepsilon,\psi)=I_{ij}^{(0)}\exp(-\int_{L_{ij}}\mu dl)(1+V_{ij}^{(0)}\exp(-\int_{L_{ij}}\varepsilon dl)\sin(\phi_{ij}^{(0)}+\psi+\partial_x\int_{L_{ij}}\delta dl)) \quad (2)$$

where $I_{ij}^{(0)}$, $V_{ij}^{(0)}$, and $\phi_{ij}^{(0)}$ denote the reference data obtained in the "blank" or air scan as: intensity, blank visibility, and reference phase (that is, phase of the Moiré reference fringe pattern) for the pixel j at readout i, respectively, $L_{ij}$ denotes the line connecting the source at projection angle/readout i and the detector pixel j at readout i, and μ, δ, ε denoting the imaging variables to be fitted to the measured interferometric intensity projection data J. The term "readout i" as used herein indicates measurements collected at different projection angles but also measurements collected at different times for the same projection direction.

The model further includes the additional fitting variable ψ for the reference phase variation of the interferometer IF, or, said differently, for the reference interference pattern caused by the interferometer in the absence of the object OB in the X-ray beam. The partial derivation $\partial_x$ is taken in the direction perpendicular to the grating orientation, that is, perpendicular to the normal to the grating plane. All mathematical equivalents of the above expression at (1a) and (2) are also envisaged herein. Also the extension of (1a) by a regularizer term or penalization term is also envisaged herein.

It is of further note that the formulation of the cost function as per (1a) has the structure of a least squares problem which is a consequence of assuming an underlying Gaussian density for the measurement. However this may not be so necessarily and other, more general structures of (1a) in the form of:

$$\Delta(\mu,\delta,\varepsilon,\psi))=\Sigma_{ij}[\Lambda(J_{i,j},I_{ij}(\mu,\delta,\varepsilon,\psi)] \quad (1b)$$

are also envisaged herein where Λ is a function that represents the statistical assumptions that are thought to govern the measurement process. In particular, statistical models other than Gaussian, e.g. Poisson, are also envisaged herein.

Applicant observed that reconstruction based on the above minimization problems helps avoid or reduce the angular blurring generated by the dedicated phase-retrieval based reconstruction in the sliding window technique for instance. Also, Applicant has found that not only does the blank scan interferometer phase (phase of the fringe pattern) $\phi_{ij}^{(0)}$ drift or fluctuate during acquisition, but also that this phase reference fluctuation is a critical (if not the most critical) parameter in terms of artifact expression. Reference phase fluctuation of the interferometer IF is addressed herein by establishing an empirical forward model as per (2) including the dedicated fitting variable ψ for possible modes of fluctuations of the blank scan phase due to drift.

In one embodiment, a constant phase offset ψ for all detector pixels and readouts j is assumed as per (2). That is, the same value is used for all pixels and all readouts j. However spatial or temporal modelling refinements are also envisaged herein.

For instance, the offset modelling may be refined in some embodiments by still assuming the same offset for all detector pixels but now with a dependency on the readout i. Notationally this can be indicated by using $\psi_i$ instead of ψ in (2). In particular, this dependency allows modeling changes of the offset from projection angle to projection angle. This can be further expanded yet by modeling the fluctuations over both dimensions of the readout i, that is, over projection direction and the time at which the collection occurs.

Of course this comes at a computational cost because the number of variables to be fitted is now increased compared to the case with constant offset.

The 1 unknown fluctuation offsets are incorporated as variables into the cost function. More specifically, as can be seen above at (2) the architecture of the forward signal model includes a first exponential factor which accounts for the attenuation. The expression in brackets (1+ . . . ) includes a term that accounts for the change in visibility. In addition there is a further, sinusoidal term factor that accounts for the contribution from refraction. The reference phase fluctuations are modeled as an additive term ψ in the argument of said sinusoidal term. The one or more phase fluctuation variables ψ are added to the experimental blank scan reference phase $\phi_{ij}^{(0)}$ to model the phase change as an additive perturbation of the blank scan $\phi_{ij}^{(0)}$. The additional term allows modeling changes caused by imperfections of the interferometer caused by mechanical deformations in response to thermal changes or simply by effect from gravity during the rotation of the interferometer during the CT scan. These mechanical effects will likely change the mutual orientation of the two gratings and hence will perturb the "detuning" earlier mentioned to establish a suitable Moiré pattern (having a period of sufficient length).

It will be understood that any mathematical equivalent of the above eq (2) is envisaged herein which includes in particular numerical approximations thereof. For instance, it will be understood by those skilled in the art that the sinusoidal expression may be replaced in approximation by a suitable polynomial expression (Taylor series expansion), etc.

While a constant phase offsets or one that varies with readout i as discussed above seems to be a sufficiently accurate model for accounting to drift in some setups, it might be too simple for larger systems with a gantry rotating at high rpms. It is therefore proposed herein, as a further spatial modeling refinement and in an alternative embodiment, to model the reference phase offset with a dependency on j, that is, there is now a dependency across pixel positions. Notationally, this modelling approach is indicated by using $\psi_j$ instead of $\psi$ in (2). This fluctuation modelling can be implemented, in a polynomial (of order n≥1) fashion, across the detector pixels j. Models other than polynomial are also possible.

If the detector is built from different modules, a slight coarsening of the pixel-to-pixel variation for the offset modelling is to vary the offset merely as a function of detector module position. The detector module offset dependency may be implemented by choosing a polynomial variation across the detector modules. Again, models other than polynomial are also possible.

In the following a further variant of the above forward model embodiments will be described. As a combination of the above spatial and/or temporal dependencies for the offset, the following refinement of (2) is also envisaged allowing now a free drift parameter for each pixel j and each readout i:

$$I_{ij}(\mu,\delta,\varepsilon,\psi_{ij})=I_{ij}^{(0)}\exp(-\int_{L_{ij}}\mu dl)(1+V_{ij}^{(0)}\exp(-\int_{L_{ij}}\varepsilon dl)\sin(\Phi_{ij}^{(0)}+\psi_{ij}+\partial_s\int_{L_{ij}}\delta dl)) \quad (3)$$

However, these many degrees of freedom as per (3) may call for some form of regularization. It is therefore envisaged in one embodiment to add to the cost function the following regularization term:

$$R_s(\psi)=\Sigma_{i,j}\Sigma_{k\in N_j}p_s(\Phi_{ij}-\psi_{ik}) \quad (4)$$

to enforce spatial smoothness where $p_s$ is a potential function operating on the differences between the fluctuations parameter $\psi$, wherein $N_j$ denotes a set of indices related to pixels in the spatial neighborhood of the pixel with index j. In one exemplary embodiment, $p_s$ is the square or the absolute value of the argument. The neighborhoods $N_j$ may represent the tiling of the detector surface into the different detector modules. Also, $p_s$ may itself vary with the neighborhoods $N_j$.

Instead of or in addition to regularizing the spatial dependencies of the offset as per (4), a temporal regularizing in order to account for phase drift in time is envisaged herein in some embodiments to enforce temporal smoothness of the phase drift modelling. Temporal variation can be achieved for instance by applying an explicit, e.g. polynomial, model of the phase drift with time, or it might be desired to add a smoothness constraint on the reconstructed phase drift. For instance, in one embodiment, a temporal regularizer term having the structure $$R_t(\psi)=\Sigma_i\Sigma_j p_t(\psi_{ij}-\psi_{i+1j}) \quad (5)$$

Is introduced. Again $p_t$ is a potential function and here differences between temporally neighboring phase drifts a per the readout index i are penalized.

Referring back to spatial smoothness, this can be also achieved if a parametric model for the spatial variation of the phases due to drift is established. For instance the phase shift due to drift might be modelled for each projection i by a polynomial with unknown coefficients. In this case, the phases $\psi_{ij}$ are fitted "indirectly" by fitting coefficients $a_{i0}$, $a_{i1}$, $a_{i2}$, ... for each readout i. Again, a temporal smoothness constraint can be imposed by adding a penalty on the coefficients of the form $$R_t(a)=\Sigma_{i,c}p_a(a_{ic}-a_{i+1c}) \quad (6)$$

where the index c runs over all coefficients.

At step S230, a single one, a selection of two, or all of the reconstructed images $\mu,\delta,\varepsilon$ are output. Output can occur during the iteration at some or each step or at the conclusion of the iterations. Outputting may include in one embodiment converting the phase contrast image into an electron density image or vice versa.

A further advantage of the processing concept described herein is that the method can easily handle distortions of the fringe pattern and that it automatically accounts for inaccuracies in the phase stepping (e.g., inaccuracies in the step increment). The optimization problem (1) above can be solved by any suitable numerical technique such as maximum likelihood approaches, conjugal gradients, Newton-Raphson etc.

It should be noted that "optimization" as used herein may not necessarily mean that the optimization results in a global optimum but may return local optima instead. Also, depending on the CPU time and other considerations it may be opportune to abort iterations before the local or global maximum is reached, for instance if differences between successive iteration results drop below a given abortion threshold.

Although in the above embodiments a dedicated second grating (G2) was used as an analyzer grating to form the interferometer, this may not necessarily be so in all embodiments. For instance, the (analyzer) grating G2 functionality can also be integrated into the detector D itself. What is more, the grating function can be entirely taken over by the detector itself by a judicial arrangement of the pixel geometry, in particular the inter-spacing between the pixels accordingly.

Figure 3:
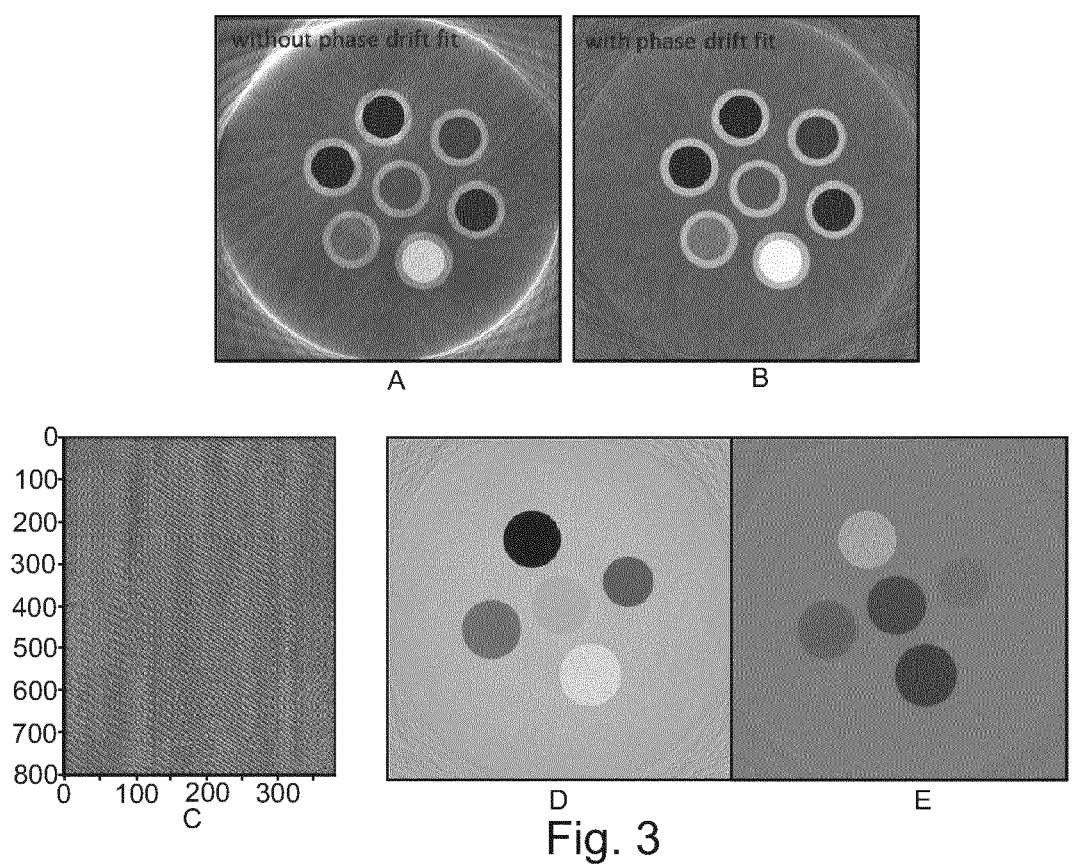
FIG. 3 shows exemplary imagery obtained by the proposed method compared to conventional imagery.

Reference is now made to FIG. 3, where experimental imagery is reproduced that shows the effectiveness of the proposed reconstruction scheme.

Pane A in FIG. 3 shows a reconstruction without phase drift fit. On the right, Pane B shows a reconstruction which includes phase drift fitting as proposed herein. As can be appreciated the reconstruction of the phantom as per Pane B is smoother and shows fewer artifacts.

Pane C of FIG. 3 shows sinogram data featuring a high-frequency fringe pattern within each projection (horizontal direction) which is shifted by a pixel from projection to projection.

Pane D shows a reconstruction according to the proposed method of the phase contrast or electron density image δ (phase contract image), and in Pane E a reconstructed attenuation image μ.

The imagery demonstrates the effectiveness of the proposed method to mitigate drifts of the fringe phase for an acquisition without any grid movement. For the imager as per the above panes C-E, focal spot sweeping was mimicked by the so-called typewriter approach where the object is translated by a pixel size between two successive projections.

As mentioned above the proposed signal processing system may run as a software routine on a workstation. In other embodiments, the proposed SPS system may be implemented as hardware in a dedicated chip, for instance, by suitably programming as an FPGA. Hardwired chip implementations are also envisaged. The chip may be integrated in video or graphics hardware of the work station or may be integrated as a processing stage in the DAS, etc.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, in particular a non-transitory storage medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A signal processing system, comprising:
at least one processor configured to:
receive interferometric projection data derived from signals acquired by an X-ray detector, said signals caused by X-ray radiation after interaction of said X-ray radiation with an interferometer and with an object to be imaged, said interferometer having a reference phase;
reconstruct one or more images of a spatial distribution of one or more physical properties of said object and fit said interferometric projection data to a signal model by adapting a plurality of fitting variables, said fitting variables including i) one or more imaging variables for the one or more images, and ii) a dedicated phase variable for a fluctuation of said reference phase; and
output said one or more images.

2. The signal processing system of claim 1, wherein the projection data has been acquired from different projection directions.

3. The signal processing system of claim 2, wherein the reference phase fluctuation is modelled by said phase variable as a constant offset independent of said different projection directions.

4. The signal processing system of claim 2, wherein the reference phase fluctuation is modeled by said phase variable as a non-constant offset that depends on said different projection directions.

5. The signal processing system of claim 1, wherein the reference phase fluctuation is modeled by said phase variable to depend on a position of a detector element of said X-ray detector.

6. The signal processing system of claim 5, wherein the detector element is a single detector pixel or a group of detector pixels.

7. The signal processing system of claim 1, wherein the phase variable includes a temporal dependency to model a change over time of said fluctuation.

8. An imaging system, comprising:
an X-ray imager comprising an interferometer and an X-ray detector configured to supply interferometric projection data; and
a signal processing system comprising:
at least one processor configured to:
receive the interferometric projection data derived from signals acquired by an X-ray detector, said signals caused by X-ray radiation after interaction of said X-ray radiation with an interferometer and with an object to be imaged, said interferometer having a reference phase;
reconstruct one or more images of a spatial distribution of one or more physical properties of said object and fit said interferometric projection data to a signal model by adapting a plurality of fitting variables, said fitting variables including i) one or more imaging variables for the one or more images, and ii) a dedicated phase variable for a fluctuation of said reference phase; and output said one or more images.

9. A signal processing method, comprising:

receiving interferometric projection data derived from signals acquired by a detector, said signals caused by radiation after interaction of said radiation with an interferometer and an object to be imaged, said interferometer having a reference phase;

reconstructing one or more images of a spatial distribution of one or more physical properties of said object by fitting, said interferometric projection data to a signal model by adapting a plurality of fitting variables, said fitting variables including i) one or more imaging variables for the one or more images, and ii) a dedicated phase variable for a fluctuation of said reference phase; and outputting said one or more images.

10. The method according to claim 9, wherein said physical property includes at least one of: i) attenuation, ii) refraction or electron density distribution, and iii) small angle scattering.

11. A non-transitory computer-readable medium having one or more executable instructions stored thereon which, when executed by at least one processor, cause the at least one processor to perform a signal processing method, comprising:

receiving interferometric projection data derived from signals acquired by a detector, said signals caused by radiation after interaction of said radiation with an interferometer and an object to be imaged, said interferometer having a reference phase;

reconstructing one or more images of a spatial distribution of one or more physical properties of said object by fitting said interferometric projection data to a signal model by adapting a plurality of fitting variables, said fitting variables including i) one or more imaging variables for the one or more images, and ii) a dedicated phase variable for a fluctuation of said reference phase; and outputting said one or more images.

* * * * *